United States Patent [19]

Reininger et al.

[11] 4,053,517
[45] Oct. 11, 1977

[54] METHOD OF ACYLATION OF PHLOROGLUCINOL

[75] Inventors: Wolfgang Reininger, Tutzing; Alfons Hartl, Germering, both of Germany

[73] Assignee: Atlantic Research Institute Limited, Nassau, Bahamas

[21] Appl. No.: 683,318

[22] Filed: May 5, 1976

[30] Foreign Application Priority Data

May 5, 1975  Germany .............................. 2519990

[51] Int. Cl.$^2$ ............................................ C07C 45/00
[52] U.S. Cl. ........................... 260/586 D; 260/586 R; 260/586 C; 260/586 P; 260/590 E; 260/591; 260/592
[58] Field of Search ............... 260/586 D, 590 E, 591, 260/592, 586 P, 586 C

[56]  References Cited
U.S. PATENT DOCUMENTS

| 3,552,975 | 1/1971 | Worden et al. | 260/586 D |
| 3,923,897 | 12/1975 | Worden | 260/586 D |
| 3,952,061 | 4/1976 | Koller et al. | 260/586 D |

FOREIGN PATENT DOCUMENTS

| 2,321,227 | 11/1974 | Germany | 260/586 D |

OTHER PUBLICATIONS

Andersen et al.I, Finn. 36,690, 2/68 (CA. 69:43521n, 1968).
Andersen et al.II, Finn. 36,691 11/67 (CA. 69:43522p 1968).
Riedl III, "Brauwiss," 85, 133 (1951).
Rosenmund et al., "Ber.", 61, 2601 (1928).
Riedl II, "Brauwiss", 4, 81 (1951).
Howard et al., "J. Chem. Soc.", 174 (1955).
Riedl I, "Ann.", 585, 38 (1954).
Collins et al., "J. Chem. Soc., Perkin I", 419 (1973).
Windisch et al., "Woschr f. Brauerei", 44, 453 (1927).
Howard, "J. Inst. Brew", 65, 414 (1959).
Ashurst et al., "J. Chem. Soc.", 1615 (1966).
Riedl, "Ber.", 96, 2870 (1957).

*Primary Examiner*—Norman Morgenstern
*Attorney, Agent, or Firm*—Browdy and Neimark

[57]  ABSTRACT

A method of acylation of phloroglucinol in the presence of a Friedel Crafts catalyst which is effected in the presence of nitromethane and dichloromethane so as to produce an acylphloroglucinol. The acylphloroglucinol is reacted with a compound selected from γ,γ-dimethyl allyl bromide and 2-methyl-but-3-ene-2-ol in the presence of a weak Lewis acid and in an organic solvent to produce a 4-desoxyhumulone which is then oxidized to produce a corresponding humulone.

23 Claims, No Drawings

METHOD OF ACYLATION OF PHLOROGLUCINOL

The invention relates to an improved method of producing humulones, and in particular to the improvement of yield in the various stages of the humulone synthesis which is known per se.

Humulones are the raw material for the production of isohumulones which impart the characteristic bitter flavor to beer. In the brewing process the isohumulones are obtained in the boiling of the wort by a conversion reaction, the so-called isomerization, from the most important group of the resins contained in the strobile of the hop, namely the humulones, which are also known under the collective name "α-acids".

The various humulones, which have the same basic chemical structure, namely that of a trisubstituted trihydroxycyclohexodienone of formula I given below, differ only in having different acyl side chains, of which the isovaleryl radical (humulone), the isobutyryl radical (cohumulone), and the 2-methylbutyryl radical (adhumulone) occur most frequently.

In the isomerization of the so-called isohumulones, which as already mentioned constitute the bitter substances present in beer, a ring is reduced in size to form a five-member ring structure, that is to say a substituted di-hydroxycyclopentenone (formula II).

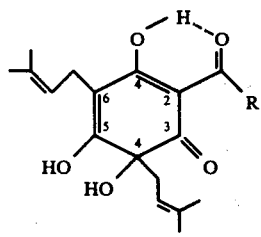

Humulone (I)

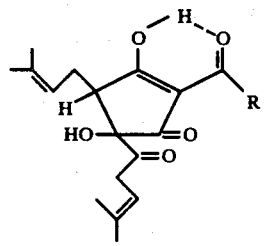

Isohumulone (II)

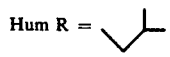
Hum R =

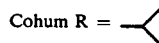
Cohum R =

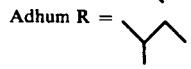
Adhum R =

The isomerization of the humulones contained in the strobiles of the hop is effected in the conventional brewing processes by boiling the hops with the wort. In this process however only about 25 to 30% of the humulones contained in the hop are utilized for forming the desired bitter substances. Various processes have therefore been developed which permit better utilization of the precursors of bitter substances which are contained in the hop. One such method is for example the "alkaline isomerization" which has been known for a long time and has been described in numerous variations, in which method the humulones are boiled with dilute alkaline solutions (see DT-PS 413,913, Windisch et al, "Woschr. f. Brauerei", 44, 453 (1927), G. A. Howard, "J.Inst. Brew.", 65, 414 (1959)).

By a more recent method humulones can be isomerized practically quantitatively to the corresponding isohumulones by the action of certain bivalent metal ions under very gentle conditions (U.S. Pat. No. 3,952,061). The resulting isomerized extract can be added in accurate doses and practically without loss in any stage of the conventional brewing process. This last-mentioned method, in which the humulones used are generally previously isolated from the hop, opens up the possibility of using synthetically produced humulones in the large scale industrial production of beer.

Although in principle the isohumulones can also be produced by total synthesis, the starting material being 1-bromo-4-methylpentyl-1,2-diene or 2-methyl-pent-2-en-4-in and the five-membered ring with the desired side chains being built up therefrom in a multistage process (P. R. Ashurst and D. R. J. Laws, "J. Chem. Soc.", 1615 (1966), and DT-PS 1,568,207), nevertheless because of its numerous complicated reaction stages and because of the extremely low yield obtained, which makes it uneconomic in practice, this method has been without importance.

The synthetic production of humulones and their conversion in a manner known per se into the desired isohumulones, on the other hand, offered a substantially greater prospect of success. Some considerable time ago W. Riedl et al described in "Brauwissenschaft", 4, 85, (1951) a method with the aid of which it is possible to product humulones synthetically in accordance with the following reaction scheme:

stage A: phloroglucinol + acid chloride → acylpholoroglucinol stage B: acylphloroglucinol + dimethylallyl bromide (prenyl bromide) → diprenyl-acylphloroglucinol (−4-desoxyhumulone)

stage C: 4-desoxyhumulone + (0) → humulone.

The yields which can be achieved by this means are nevertheless too low (the total yield of humulone referred to the phloroglucinol used amounts to only about 0.3%) for it to be possible to produce economically the humulones required for carrying out the brewing process. The economic synthesis of humulone (this expression is used hereinbelow for the more general group of "humulones") in this way would be possible only if the yields in the individual reaction stages could be substantially improved.

The problem underlying the invention is therefore that of indicating an improved process for the production of humulone, with the aid of which it is possible, starting with phloroglucinol, to produce humulone with a total yield such that the synthetic production of humulone is economically interesting in comparison with the production of humulone from natural hops.

The object of the invention is an improved method of producing humulone by acylation of phloroglucinol with the aid of an acid chloride and in the process of AlCl₃ as catalyst (stage A), followed by alkylation of the resulting acylphloroglucinol with γ, γ-dimethylallyl bromide (prenyl bromide) or with 2-methyl-but.-3-en-2-ol and zinc chloride, thereby forming diprenyl-acylphloroglucinol (4-desoxyhumulone) (stage B), which in a manner known per se is converted by oxidation or hydroxylation into humulone (stage C), which method is characterized in that stage A is carried out in the presnce of nitromethane and with the aid of dichloromethane as solvent, and that the alkylation in stage B is effected in an organic solvent with the aid of a weak Lewis acid, preferably of $ZnCl_2$ in dioxane or ether/methylene chloride or $POCl_2$ in methylene chloride or of an acid ion exchanger, preferably acid zeolites, such as for example KSF catalyst or K-10 of Girdler-Sudchemie, instead of boron trifluoride-dietherate, as catalyst.

A decisive step forward in respect of the economy of the process is achieved according to a preferred embodiment of the invention in which the alkylation in stage B is effected by blocking an OH group of the acylphloroglucinol by means of a protective group which can easily be split off again after the alkylation without damaging the molecule. It is here immaterial whether the OH group in the ortho position or that in the para position is protected. The mono-OH protected acylphloroglucionol can be quantitatively prenylated to 4-desoxyhumulone. This procedure is novel in this field.

The method of the invention, which in all its possible variations is comprehensively represented, together with the boron humulone synthesis process, in the accompanying reaction plan, is explained more fully below with reference to the various stages of the synthesis.

Stage A: Acylation of phloroglucinol

The acylation of phloroglucinol utilizing the Friedel-Crafts-catalayst $AlCl_3$ is known per se.

Hitherto phloroglucinol in nitrobenzene was reacted with the desired acid chloride with the addition of from 3 to 4 mole equivalents of $AlCl_3$. The yields achieved were however very low, because the phloracylphenones produced were decomposed during the necessary removal of large amounts of sparingly volatile nitrobenzene (K. W. Rosenmund, H. Lohfert, "Ber." 61,2601 (1928), W. Riedl, "Brauwiss", 4, 81 (1951)). Subsequently a large proportion of the nitrobenzene was replaced by carbon disulphide (W. Riedl, "Ann.", 585, 38 (1954), G. A. Howard, J. R. A. Pollock and A. R. Tatchell, "J. Chem. Soc.", 174 (1955)), but in all cases the average yields amounted to 50% at the most.

It has been found that the yield in that stage can be very substantially improved if nitrobenzene is replaced by nitromethane and if methylene chloride is used as solvent instead of carbon disulphide. In this case the nitromethane need be added only in an amount of from 1.5 to 2 mole equivalents, while at the same time the amount of aluminum chloride required can be reduced to 1.5-2 mole equivalents. If less than 1.5 mole equivalent of $AlCl_3$ is used, the yield will be reduced, while the use of more than 2.5 mole equivalents of $AlCl_3$ will entail the production of resin-like by-products, which make the working-up of the reaction mixture difficult.

It is assumed that through the use of nitromethane instead of nitrobenzene the phloroglucinol-aluminum chloridenitromethane complex occuring as intermediate product is formed more easily because of the reduced steric hindrance and reacts more easily with the acid chloride-aluminum chloride complex which is likewise formed.

Stage A of the process of the invention can for example be carried out by suspending one mole of phloroglucinol and from 1.5 to 2 moles of anhydrous aluminum chloride in ten times the amount of dichloromethane, adding from 1.5 to 2 moles of nitromethane drop by drop while stirring and cooling, and heating the mixture for 5 minutes at from 35° to 40° C, which entails intensive generation of HCl. 1 mole of acid chloride is then added drop by drop and the mixture boiled with reflux for 10 minutes. Decomposition of the resulting complex with ice/HCl, distilling off the methylene chloride and nitromethane, and recyrstallization of the resulting product from water enable the desired product to be obtained in a yield between 70 and 95%, on the average higher than 80%. When straight-chain acid chlorides are used, the yields are generally above 90%.

If stage A of the method of the invention is carried out in the manner described above, the following advantages are thereby achieved.

1. the yields are substantially higher than when the conventional process is employed;
2. the products obtained are substantially purer, since less by-products are formed:
   a. because of the lower reaction temperature resulting from the use of methylene chloride as solvent,
   b. because the nitromethane is distilled off more rapidly at a low temperature, and
   c. because of a simplification of the working-up of the reaction mixture because of the smaller amount of solvents and aluminum trichloride.
3. the highly poisonous solvents nitrobenzene and carbon disulphide are replaced by the comparatively only slightly toxic nitromethane and incombustible methylene chloride; and
4. the consumption of chemicals is generally lower.

Stage B: Alkylation of acylphloroglucinol to 4,6-diprenylacylphologlucinol

The alkylation of acylphloroglucinol with γ, γ-dimethylallyl bromide (prenyl bromide) under basic conditions is already known. It was first described by Riedl. It produces a complex mixture of differently alkylated compounds, the proportion of 4,6-diprenyl-isovalerylphloroglucinol being under 10% even in the most favorable case, while in addition this product must be isolated by applying an expensive purification process (W. Riedl and H. Hubner, "Ber.", 96, 2870 (1957)).

The reason for the low yields of diprenyl-acylphloroglucinol in the presence of strong bases is probably that the monoprenyl compound is first formed and under alkaline conditions produces an anion on the already substituted C atom. The next prenyl radical then occurs preferentially on the already substituted C atom. The diprenyl compound formed in this manner is very easily further prenylated on the still free C atom, while a fourth prenyl radical may also still occur. The 4,6-diprenyl-acylphloroglucinol formed is also very readily further prenylated, forming lupulone analogues.

By direct alkylation of acylphloroglucinol with 2-methyl-but-3-ene-2-ol in the presence of boron trifluorideether complex as catalyst, it was possible to increase the yield of the desired final product, but it was still under 20% (E. Collins and P. V. R. Shannon, "J. Chem. Soc. Perkin I", 419 (1973)).

In the case of alkylation under acid conditions it is true that the situation is more favorable, because the aromatic form of acylphloroglucinol is then preferred over the dienone form, but the difficulty occurs here that the double bonds of the prenyl radicals can easily be protonated by the protons present in the solution. Cyclization then occurs with the formation of benzopyran or benzofuran compounds, which reduce the yield, and once again a very complex mixture of different compounds is formed with can be split up only with difficultly.

It has now been found that directed prenylation can be achieved in stage B of the process of the invention by working in an organic solvent in the presence of a relatively weak Lewis acid as catalyst, for example in the presence of $EnCl_2$ in dioxane or ether/methylene chloride or in the presence of $POCl_3$ in methylene chloride, or with an acid ion exchanger, preferably acid zeolites, for example KSF or X-10 catalyst of Girdler-Sudchemie, instead of the boron trifluoride-dietherate complex.

In practice 2-methyl-but-3-ene-2-ol in anhydrous dioxane is added drop by drop to a suspension of acylphloroglucinol and catalyst, while stirring, and stirring is continued for some time at room temperature or slightly elevated temperature. The mixture is then extracted with water, a soda solution, and then with ether. The yield of 4,6-diprenylacylphloroglucinol can then be considerably increased in relation to the known performance of stage B, while less by-products are also produced. Consequently yields of about 40% of the theoretical can be achieved.

A substantial improvement of the yield in this stage and a further simplification of the process can be achieved by blocking one OH group - which may be either an o-OH group of a p-OH group, with a protective group. The phloroglucinol molecule, which is very reactive because of its numerous possibilities of tautomerism, is thereby partly deactivated so that directed 2,4-prenylation is possible. This is probably also one of the reactions which occur in nature in the hop plant, wherein monoprenyl-acylphloroglucinol is likewise first formed and is bound up by an OH group to an enzyme, thereupon reaction with dimethylaliyl pyrophosphate (F. Drawet, J. Beier, "Brauwiss.", 26, 357 (1973)).

Only those protective groups which can be easily split off again without changing the molecule may be used according to the invention. This means that those protective groups which have to be split off by means of strong acids (such as methyl ether) or hydrogenolytically (such as benzyl ether) cannot be used. Acetal-like radicals, such as methoxymethyl ether or dihydropyranyl ether, which can be split off with weaker acids, or esters containing for example acetyl or benzoyl radicals, which can be split off with weak bases, and also silyl ethers which can even be split off with water, are suitable.

The number of protective groups which are suitable according to the invention is extremely large and in no way restricted to the examples mentioned above. In practice, however, only those protective groups which can be produced cheaply and are simple to use will be employed. This includes in particular methoxymethyl ethers, benzoates, and, preferably, acetates.

It is true that it is not quite simple to produce an acylphloroglucinol in which only one OH group is blocked by a protective group, because as a rule the protective group occurs simultaneously in more than one or in all three OH groups; it has however been found that this difficulty can be overcome by partially saponifying, to the stage of the desired mono-blocked product, the triacetyl compounds which are thus formed and which are provided with protective groups. While doubly and triply blocked acylphloroglucinols are undesirable because they are too intensively deactivated and no longer react with the prenylation medium, in the case of the singly blocked acylphloroglucinols it is not important whether the protective group is in the ortho position or in the para position in relation to the acyl groups. In both cases the subsequent prenylation leads to the desired diprenyl compounds, with quantitative yield.

If desired, the mono-, di-, and tri-acetates can be isolated and identified by chromatographic separation of a partial hydrolysate of tri-O-acetyl-phloroacylophenone on acetylated polyamide with methylene chloride/acetone.

An important feature of the present invention therefore consists in that when mono-O-protected acylphloroglucinols are used the desired 4-desoxyhumulones are obtained quantitatively in the prenylation process, irrespective of the position of the protective group. Even if di-O-protected acylphloroglucinols should be present during the reaction, they will not be wasted, because they are not prenylated and after complete saponification can be recovered as unchanged starting material.

An important advantage of carrying out stage B in the manner described above therefore consists in that it is thus possible to recover the expensive acylphloroglucinols which have not been converted into 4-desoxyhumulones, so that they can be used again for the reaction. Stage B can be carried out in the manner proposed according to the invention, simply and without expensive purification and separation operations. In greater detail, stage B of the method of the invention is carried out, for example, in the following manner:

Acylphloroglucinol is stirred for 2 hours at from 50° to 60° C with a slight excess of acetic anhydride in the presence of anhydrous sodium acetate. The acetylation continues until no further free acylphloroglucinol is present. The mixture is then mixed with ten times the amount of water, stirred for about one hour to the desired degree of saponification determined empirically by thin-layer chromatography, water is again added, and the mixture is extracted with methylene chloride. The dried methylene chloride phase is stirred with 2 moles of 2-methyl-but-3-ene-2-ol and 2 moles of anhydrous zinc chloride, referred to the acylphloroglucinol, for 2 hours at room temperature. The mixture is then extracted with water and thereupon with a saturated solution of soda. After acidification, the 4,6-diprenylacylphloroglucinols are first extracted with hexane and then the unreacted acylphloroglucinols are extracted with ether. The unreacted acylphloroglucinols are reused in the reaction.

Stage C: Oxidation or hydroxylation of 4-desoxyhumulone to humulone

Stage C of the method of the invention, that is to say the conversion into humulone of the 4-desoxyhumulone obtained in stage B, is carried out in a manner known per se. For this purpose the recently discovered methd of hydroxylation of substituted acylphloroglucinols (DT-OS 2, 321,227) is expendiently applied, because the atmospheric oxidation in the presence of lead acetate (Wollmer oxidation), as described in literature, has been found uneconomical with yields of only 3 to 6% of the theoretical. In this method described in DT-OS Pat. No. 2,321,227, 4-desoxyhumulone is reacted with substances which are able to form hydroxyl cations, such as for example per acids, hydroperoxides, N oxides, or oxygen activated by dyestuffs. The yields of this process are from 70 to 80%, so that in all stages of the process of the invention yields are obtained which permit synthesis of humulone on an industrial scale by means of an economic method.

The invention is explained more fully by the following examples.

EXAMPLE 1

0.05 mole of phloroglucinol and 0.1 mole of anhydrous aluminum trichloride are suspended in 50 ml of methylene chloride. 0.1 mole of nitromethane is then rapidly added drop by drop, while stirring, the temperature thus rising to about 33° C, the phloroglucinol and AlCl$_3$ being dissolved, and HCl escaping. The mixture is heated for a few minutes of 40° C and within the space of a few minutes 0.05 mole of n-butyric acid chloride is added drop by drop. After boiling for 10 minutes with reflux, decomposition is effected with ice/hydrochloric acid, the methylene chloride and nitromethane are evaporated off, and the product is extracted with ether. In this way a resin is obtained which has a faint yellow coloration and which, as shown by gas chromatography, consists of 97% of monobutyl phloroglucinol (phlor-n-butyrophenone). After recrystallization from water, white needles are obtained, M.P. 184° C, with a yield of 90%.

The compounds indicated below can be obtained by the same process, with the yields indicated:
phlor-propiophenone, M.P. 174° C, yield 83%
phlor-n-valerophenone, M.P. 153° C, yield 85%
phlor-n-caprophenone, M.P. 131° C, yield 81%
phlor-iso-butyrophenone, M.P. 141° C, yield 82%
phlor-iso-valerophenone, M.P. 145° C, yield 80%
phlor-benzophenone, M.P. 164° C, yield 83%

EXAMPLE 2

3.92 g (0.02 mole) of phlor-isobutyrophenone are dissolved in 50 ml of dioxane and boiled for 1 hour with reflux together with 6 g of anhydrous ZnCl$_2$ and 12 ml of 2-methylbutene-3-ol-2. After cooling, the mixture is decomposed with 500 ml of ice water and extracted with ether. Gas chromatography shows that the resulting residue consists of 40% of 4-desoxy-cohumulone, 40% of monoprenyl-phlor-isobutylphenone, and 20% of phlor-iso-butyrophenone.

For purification purposes the product is subjected to chromatography on acetylated polyamide MN-6-Ac with hexane/ethyl acetate (1 to 10%).

After recrystallization from pentane the 4-desoxycohumulone is obtained in this manner in the form of yellowish prisms, M.P. 73° C.

EXAMPLE 3

The process of Example 2 is repeated, 2 g of catalyst KSF or KP 10 of Gridler Sudchemie being this time used instead of ZnCl$_2$. The reaction time is in this case lengthened to 2 hours, and the same yields are obtained as in Example 2.

EXAMPLE 4

1.96 g (0.01 mole) of phlor-iso-butyrophenone and 4 g of anhydrous ZnCl$_2$ are suspended in 50 ml of methylene chloride, with heating, and 3 ml of 2-methylbutene-3-ol-2 in 5 ml of methylene chloride are added drop by drop. The mixture is boiled for 30 minutes with reflux, cooled, and shaken up with water. From the methylene chloride phase a resin is obtained which consists of 50% 4-desoxy-cohumulone and 50% colupulone. The product is worked up in the same way as in Example 2.

EXAMPLE 5

The process of Example 4 is repeated, but this time 3 ml of POCl$_3$ are used instead of ZnCl$_2$, and the mixture is stirred at room temperature for 60 minutes. The same yields are obtained as in Example 4.

EXAMPLE 6

10.5 g (0.05 mole) of phlor-iso-valerophenone are stirred for 2 hours at 60° C with 500 mg of anhydrous sodium acetate and 20 ml of acetic anhydride. The mixture is mixed with 20 ml of water and stirring continued for about 1 hour. The exact end point is determined by chromatography. Fartial saponification thus occurs in the solution buffered with sodium acetate, without free acylphloroglucinol being formed. The product is then extracted with 50 ml of methylene chloride and the extract is dried.

The methylene chloride solution is mixed with 15 g of ZnCl$_2$ and 12 ml of 2-methylbutene-3-ol-2 and stirred at room temperature for 2 hours. The mixture is then washed with water and extracted with a saturated sodium carbonate solution. After 2 hours the soda extract is acidified and extracted with hexane. After drying and concentration, the 4-desoxyhumulone crystallizes out of the hexane solution. The aqueous phase is extracted with ether in order to recover the unreacted acylphloroglucinol.

EXAMPLE 7

9.8 g (0.05 mole) of phlor-isobutylophenone are suspended in 23 ml of acetic anhydride, mixed with 250 mg of anhydrous sodium acetate, and stirred for 2 hours at 60°. 20 ml of water are then added. When allowed to stand overnight in a refrigerator, the tri-O-acetylphlor-iso-butyrophenone crystallizes out, M.P. 91° C (methanol), yield 78%.

EXAMPLE 8

10.5 g of phlor-iso-valerophenone are stirred for 2 hours at 60° C with 500 mg of sodium acetate and 20 ml of acetic anhydride. 20 ml of water are then added, the mixture is stirred for an hour, and extracted with 50 ml of methylene chloride. The methylene chloride solution is washed with water, dried, and separated by chromatography on acetylated polyamide MN-6-Ac with methylene chloride. The fractions consisting of phloroiso-valerophenone-5-monoacetate (faintly yellow crystals, after recrystallization from CH$_2$Cl$_2$ or benzene, M.F. 120° C), and phlor-iso-valerophenone-3-monoacetate are thus obtained The following compounds can be produced by the same method:
Phlor-iso-butyrophenone-3-monoacetate, colorless crystals, M.P. 125° C and
phlor-iso-butyrophenone-5-monoacetate, yellowish crystals, M.P. 127° C (benzene).

The structure of these compounds is confirmed by the NMR and IR spectra.

EXAMPLE 9

This example shows the entire process for the production of humulone.

12.6 g of phloroglucinol and 26.7 g of anhydrous aluminum trichloride are suspended in 100 ml of methylene chloride, and 12 ml of nitromethane are added rapidly drop by drop, while stirring. The mixture is heated for a few minutes at 40° C and then within a few minutes is fixed with 10.7 g of iso-butyric acid chloride. After boiling for 10 minutes with reflux, the mixture is acidified with the addition of ice. The solvents are evaporated off in vacuo, the aqueous phase is extracted with ether, and the ether extract is concentrated.

The concentration residue is taken up in 40 ml of acetic anhydride, mixed with 1 g of anhydrous sodium acetate, and stirred for two hours at 60° C. After the addition of 40 ml of water, the stirring is continued for 1 hour at room temperature. The mixture is then extracted with 100 ml of methylene chloride, the extract is dried and mixed with 30 g of $ZnCl_2$ and 25 ml of 2-methyl-butene-3-ol-2 and stirred for 2 hours at room temperature. The reaction mixture is then washed with water and extracted with saturated sodium carbonate solution. After 2 hours the mixture is acidified and extracted with hexane and ether. The ether extract is re-used in the application stage of the process.

The hexane phase is concentrated, the residue dissolved in 150 ml of methanol and 40 ml of 10% sodium hydroxide solution, and mixed with 10 ml of 80% tert.-butyl-hydroperoxide while stirring. As soon as the color of the reaction mixture lightens (about 2 hours), the reaction is complete. The mixture is diluted with water, extracted with hexane, acidified, and the cohumulone is extracted with ether. Total yield about 50%.

EXAMPLE 10 benzoate blocking group 16.8 g (0.1 mole) phloroacetophenone are dissolved in 100 ml anhydrous ether and added with 60 ml pyridine. Then 60 g (about 0.5 mole) of benzoyl chloride are added drop by drop in such a manner that the ether is brought to sight boiling by the heat of reaction. Then the mixture is additionally refluxed for 3 hours. The solution is then extracted 2 times with 50 ml diluted $H_2SO_4$ (0.5 N), dried and concentrated. One gets tri-O-benzoyl-phloroacetophenone in a yield of more than 90% as oil which crystallizes slowly.

After recrystallization from ethanol the product is white needles with a melting point of 114° to 116° C.

2.4 g (5 mole) tri-O-benzoyl-phloroacetophenone are warmed in 30 ml methanol to 55° and then added with 9 ml saturated $NaHCO_3$-solution (10 mole). The saponification is followed chromatographically. After about 1½ hours the maximum concentration in monobenzoate is attained. The mixture is diluted with 20 ml water and slightly acidified on which there is a precipitation which is separated and recrystallized from dioxane/water = 1:1 to give colorless platens with a melting point of 203° C.

Mono-O-benzoyl-phloroacetophenone is reacted with $ZnCl_2$ and 2-methyl-buten-3-ol-2 corresponding to examples 6 or 9 in a practically quantitative manner to give diprenyl-phloroacetophenone.

EXAMPLE 11 reaction with prenylbromide 10.5 g (0.05 mole) phlor-iso-valerophenone and 2 g $ZnCl_2$ are suspended in 50 ml of a mixture of ether/methylene chloride = 1:1.

While adding 7,5 g γ, γ-dimethylallylbromide (prenylbromide), dissolved in 5 ml methylene chloride, drop by drop the reaction mixture is dissolved for 1 hour and then cooled and extracted with water.

Further processing and isolation is done as shown in example 2.

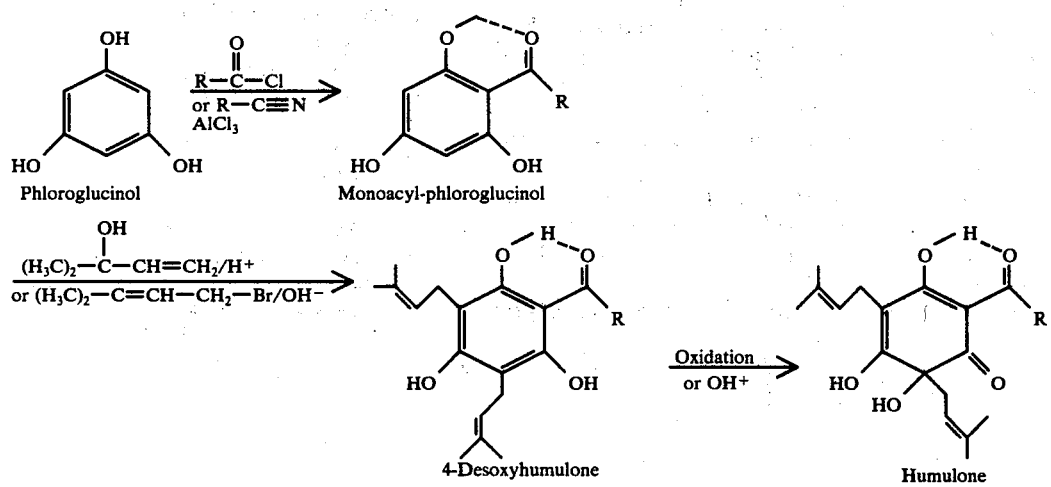

What is claimed is:

1. In a method of producing an acylphloroglucinol for use in the preparation of humulone comprising acylation of phloroglucinol in the presence of a Friedel Crafts catalyst so as to produce said acylphloroglucinol, the improvement comprising carrying out said acylation in the presence of at least 1.5 moles of nitromethane per mole of phloroglucinol and in dichloromethane as solvent.

2. The method of claim 1 wherein acylation is effected with an acid chloride.

3. The method of claim 2 wherein the Friedel Crafts catalyst is aluminum chloride.

4. The method of claim 3 wherein from 1.5 to 2 moles of aluminum chloride are used per mole of phloroglucinol.

5. The method of claim 4 wherein from 1.5 to 2.5 moles of nitromethane are used per mole of phloroglucinol.

6. The method of claim 3 wherein the acylphloroglucinol obtained is reacted with a compound selected from the group consisting of γ, γ-dimethylallyl bromide and 2 - methyl - but -3-ene - 2 -ol in the presence of a weak Lewis acid catalyst selected from the group conisting of $ZnCl_2$, $POCl_3$ and an acid ion exchanger in an organic solvent selected from the group consisting of dioxane, methylene chloride and ether/methylene chloride so as to produce a 4-desoxyhumulone and wherein said 4 - desoxyhumulone is oxidized so as to produce a humulone.

7. The method of claim 6 wherein said 4 - desoxyhumulone is oxidized by an oxidizing agent selected from the group consisting of a per acid, hydroperoxide, N - oxide and oxygen activated by a dyestuff.

8. The method of claim 2 wherein said acid chloride is an alkanoyl chloride having from 3 to 6 carbon atoms.

9. The method of claim 2 wherein said acid chloride is benzoyl chloride.

10. In a method of producing a 4 - desoxyhumulone for use in the preparation of a humulone comprising alkylation by reacting an acylphloroglucinol with a compound selected from the group consisting of γ, γ-dimethylallyl bromide and 2 - methyl - but - 3 -ene - 2 - ol so as to produce said 4 -desoxyhumulone, the improvement comprising carrying out said alkylation reaction in an organic solvent selected from the group consisting of dioxane, methylene chloride and ether/methylene chloride, in the presence of a weak Lewis acid catalyst selected from the group consisting of $ZnCl_2$, $POCl_3$ and acid ion exchanger.

11. The method of claim 10 wherein said weak Lewis acid catalyst is $ZnCl_2$.

12. The method of claim 11 wherein said organic solvent is dioxane or ether/methylene chloride.

13. The method of claim 10 wherein said weak Lewis acid catalyst is $POCl_3$.

14. The method of claim 13 wherein said organic solvent is methylene chloride.

15. The method of claim 10 wherein said weak Lewis acid catalyst is an acid ion exchanger.

16. The method of claim 15 wherein said acid ion exchanger is an acid zeolite.

17. The method of claim 10, further including a preliminary step of protecting one of an OH group in ortho position and an OH group in a para position in said acylphloroglucinol by a blocking group which can be easily split off again after said alkylation reaction.

18. The method of claim 17 wherein said blocking group is selected from a class of blocking groups which can be split off by water, weak acids or weak bases.

19. The method of claim 18 wherein said blocking group is selected from the group consisting of methoxymethylether, dihydropyranyl ether, sily ether, acetyl and benzoyl radical.

20. The method of claim 17 wherein said mono O - protected acylphloroglucinol is produced by first preparing a di - O - protected acylphloroglucinol and then mildly saponifying.

21. The method of claim 20 wherein after reaction of the mono - O - protected acylphloroglucinol to produce the 4 - desoxyhumulone, said 4 - desoxyhumulone is oxidized so as to produce humulone, and any blocking groups still present in said humulone are split off by saponification.

22. The method of claim 21 wherein any unreacted acylphloroglucinol is recovered for recycling in said method.

23. The method of claim 21 wherein said 4 - desoxyhumulone is oxidized by an oxidizing agent selected from the group consisting of a per acid, hydroperoxide, N - oxide and oxygen activated by a dyestuff.

* * * * *

UNITED STATES PATENT AND TRADEMARK OFFICE
CERTIFICATE OF CORRECTION

PATENT NO. : 4,053,517
DATED : October 11, 1977
INVENTOR(S) : REININGER et al.

It is certified that error appears in the above-identified patent and that said Letters Patent are hereby corrected as shown below:

Title page, column 2, line 6, " "Brauwiss,," 85," should read --"Brauwiss, 4, 85,--

Column 1, line 19, "hydroxycyclohexodienone" should read --hydroxycyclohexadienone-- line 24, "of" should read --to-- column 2, line 41, "(—4-desoxyhumulone)" should read --(=4-desoxyhumulone)-- line 62, "process" should read --presence-- column 3, line 1, "humulone" should read --humulones-- line 24, "boron" should read --known-- line 45, after "It has" insert --now-- line 59, "chloridenitromethane" should read --chloride-nitromethane-- column 4, line 33, "4,6-diprenylacylphologlucinol" should read --4,6-diprenylacylphloroglucinol-- column 5, line 2, "difficultly" should read --difficulty-- line 7, "EnCl$_2$" should read --ZnCl$_2$-- line 10, "X-10" should read --K-10-- line 17, "soda" should read --sodium carbonate--

UNITED STATES PATENT AND TRADEMARK OFFICE
CERTIFICATE OF CORRECTION

PATENT NO. : 4,053,517
DATED : October 11, 1977
INVENTOR(S) : REININGER et al.

It is certified that error appears in the above-identified patent and that said Letters Patent are hereby corrected as shown below:

Column 5, line 33, "bound up by" should read --bound by-- line 34, "reaction" should read --reacting-- line 35, "Drawet" should read --Drawert-- column 6, line 45, "soda" should read "sodium carbonate-- line 56, "methd" should read --method-- line 62, delete "Pat. No."

column 7, line 13, "of" should read --at-- line 21, "monobutyl" should read --monobutyryl-- line 43, "monoprenyl-phlor-isobutylphenone" should read --monoprenyl-phlor-isobutyrophenone-- line 54, "KP 10" should read --K-10--; "Gridler Sudchemie" should read --Girdler Südchemie-- column 8, line 14, "Fartial" should read --Partial-- line 31, "phlor-isobutylophenone" should read --phlor-isobutyrophenone-- column 9, line 1, "fixed" should read --mixed-- line 6, "concentration" should read --concentrated-- line 18, "application" should read --acetylation--

UNITED STATES PATENT AND TRADEMARK OFFICE
CERTIFICATE OF CORRECTION

PATENT NO. : 4,053,517
DATED : October 11, 1977
INVENTOR(S) : REININGER et al.

It is certified that error appears in the above-identified patent and that said Letters Patent are hereby corrected as shown below:

column 9, line 63, "(5 mole)" should read --(5 mmole)-- line 64, "55°" should read --55° C-- line 65, "(10 mole)" should read --(10 mmole)-- column 10, line 17, "dissolved" should read --refluxed--

Signed and Sealed this

Twenty-ninth Day of August 1978

[SEAL]

Attest:

RUTH C. MASON
Attesting Officer

DONALD W. BANNER
Commissioner of Patents and Trademarks